(12) United States Patent
Racenet et al.

(10) Patent No.: US 8,678,264 B2
(45) Date of Patent: Mar. 25, 2014

(54) SURGICAL INSTRUMENT WITH ELONGATED CHANNEL

(75) Inventors: Danyel (Tarinelli) Racenet, Middletown, CT (US); Thomas Wenchell, Durham, CT (US); Keith L. Milliman, Bethel, CT (US)

(73) Assignee: Covidien LP, Mansfield, MA (US)

(*) Notice: Subject to any disclaimer, the term of this patent is extended or adjusted under 35 U.S.C. 154(b) by 49 days.

(21) Appl. No.: 12/486,826

(22) Filed: Jun. 18, 2009

(65) Prior Publication Data

US 2010/0001037 A1 Jan. 7, 2010

Related U.S. Application Data

(60) Provisional application No. 61/078,460, filed on Jul. 7, 2008.

(51) Int. Cl.
*A61B 17/068* (2006.01)

(52) U.S. Cl.
USPC ........................ 227/175.1; 600/104; 227/179.1

(58) Field of Classification Search
USPC ............... 227/175, 175.1, 19, 179.1; 600/104
See application file for complete search history.

(56) References Cited

U.S. PATENT DOCUMENTS

| | | | |
|---|---|---|---|
| 5,403,326 A * | 4/1995 | Harrison et al. | 606/139 |
| 5,483,951 A * | 1/1996 | Frassica et al. | 600/104 |
| 5,868,760 A | 2/1999 | McGuckin, Jr. | |
| 6,083,241 A | 7/2000 | Longo et al. | |
| 6,102,271 A | 8/2000 | Longo et al. | |
| 6,119,913 A | 9/2000 | Adams et al. | |
| 6,126,058 A | 10/2000 | Adams et al. | |
| 6,142,933 A | 11/2000 | Longo et al. | |
| 6,179,195 B1 | 1/2001 | Adams et al. | |
| 6,241,140 B1 | 6/2001 | Adams et al. | |
| 6,264,086 B1 | 7/2001 | McGuckin, Jr. | |
| 6,302,311 B1 * | 10/2001 | Adams et al. | 227/176.1 |
| 6,343,731 B1 | 2/2002 | Adams et al. | |
| 6,478,210 B2 | 11/2002 | Adams et al. | |
| 6,585,144 B2 | 7/2003 | Adams et al. | |
| 6,601,749 B2 | 8/2003 | Sullivan et al. | |
| 6,629,630 B2 | 10/2003 | Adams | |
| 6,632,227 B2 | 10/2003 | Adams | |
| 6,695,198 B2 | 2/2004 | Adams et al. | |
| 6,820,791 B2 | 11/2004 | Adams | |
| 6,827,246 B2 | 12/2004 | Sullivan et al. | |
| 6,840,423 B2 | 1/2005 | Adams et al. | |
| 6,866,178 B2 | 3/2005 | Adams et al. | |
| 6,874,669 B2 | 4/2005 | Adams et al. | |
| 6,959,851 B2 | 11/2005 | Heinrich | |
| 7,083,630 B2 | 8/2006 | DeVries et al. | |
| 7,090,684 B2 | 8/2006 | McGuckin et al. | |
| 7,810,690 B2 * | 10/2010 | Bilotti et al. | 227/175.1 |
| 8,181,840 B2 * | 5/2012 | Milliman | 227/179.1 |
| 2002/0020732 A1 | 2/2002 | Adams et al. | |
| 2002/0047036 A1 | 4/2002 | Sullivan et al. | |
| 2002/0063143 A1 | 5/2002 | Adams et al. | |

(Continued)

*Primary Examiner* — Andrew M Tecco (57) ABSTRACT

A surgical instrument including a handle assembly, an elongated body portion, a head portion and an elongated channel. The elongated body portion extends distally from the handle assembly. The head portion is disposed adjacent a distal end of the elongated body portion and includes an anvil assembly and a shell assembly. The elongated channel includes a proximal opening and a distal opening. The proximal opening is disposed distally of a proximalmost end of the handle assembly and proximally of the shell assembly. The distal opening is disposed on the shell assembly.

28 Claims, 7 Drawing Sheets

(56) References Cited

U.S. PATENT DOCUMENTS

| | | |
|---|---|---|
| 2003/0019905 A1 | 1/2003 | Adams et al. |
| 2003/0127491 A1 | 7/2003 | Adams et al. |
| 2003/0132267 A1 | 7/2003 | Adams et al. |
| 2003/0192937 A1 | 10/2003 | Sullivan et al. |
| 2004/0134964 A1 | 7/2004 | Adams et al. |
| 2004/0193184 A1 | 9/2004 | Laufer et al. |
| 2004/0232198 A1 | 11/2004 | Adams et al. |
| 2005/0145675 A1 | 7/2005 | Hartwich et al. |
| 2005/0205640 A1* | 9/2005 | Milliman .................. 227/176.1 |
| 2006/0151568 A1 | 7/2006 | Weller et al. |
| 2006/0155308 A1* | 7/2006 | Griego ......................... 606/142 |
| 2006/0191975 A1* | 8/2006 | Adams et al. ............. 227/180.1 |
| 2006/0241692 A1 | 10/2006 | McGuckin, Jr. et al. |
| 2007/0023475 A1* | 2/2007 | Csiky ........................ 227/175.1 |
| 2007/0233161 A1 | 10/2007 | Weller et al. |

* cited by examiner

SURGICAL INSTRUMENT WITH ELONGATED CHANNEL

This application claims priority to provisional application Ser. No. 61/078,460, filed Jul. 7, 2008, the entire contents of which are incorporated herein by reference.

BACKGROUND

1. Technical Field

The present disclosure relates generally to a surgical stapling device for applying surgical staples to body tissue. More particularly, the present disclosure relates to a surgical stapling device suitable for performing circular anastomosis and/or treatment to internal walls of hollow tissue organs.

2. Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 6,945,444, 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with attached anvil head is mounted to the distal end of the instrument adjacent the staple holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil. An annular knife is concurrently advanced to core tissue within the hollow organ to free a tubular passage within the organ.

Besides anastomosis of hollow organs, surgical stapling devices for performing circular anastomosis have been used to treat internal hemorrhoids in the rectum. Typically, during use of a circular stapling device for hemorrhoid treatment, the anvil head and the staple holding component of the surgical stapling device are inserted through the anus and into the rectum with the anvil head and the staple holding component in an open or unapproximated position. Thereafter, a pursestring suture is used to pull the internal hemorrhoidal tissue towards the anvil rod. Next, the anvil head and the staple holding component are approximated to clamp the hemorrhoid tissue between the anvil head and the staple holding component. The stapling device is fired to remove the hemorrhoidal tissue and staple the cut tissue.

In certain situations, it is desirable to use an endoscope and/or an illumination device while performing an anastomosis. In such circumstances, surgeons typically create an additional opening in the patient to allow passage of such instruments.

Accordingly, it would be advantageous to provide a surgical stapling instrument which would enable illumination or visualization without requiring an additional opening in the patient. It would also be advantageous if such instrument could further enable introduction of fluids or other instrumentation without requiring removal of the instrument or requiring additional clamping and equipment.

SUMMARY

The present disclosure relates to a surgical stapling instrument including a handle assembly, an elongated body portion, a head portion and an elongated channel. The elongated body portion extends distally from the handle assembly. The head portion is disposed adjacent a distal end of the elongated body portion and includes an anvil assembly and a shell assembly. The elongated channel includes a proximal opening and a distal opening. The proximal opening is disposed distally of a proximalmost end of the handle assembly and proximally of the shell assembly. The distal opening is disposed on the shell assembly. In an exemplary embodiment, the proximal opening is disposed proximally of a midpoint of the elongated body portion and distally of the handle assembly.

The present disclosure also relates in another aspect to a method of performing a surgical procedure. The method includes the step of providing a surgical instrument including a handle assembly, an elongated body portion, a head portion and an elongated channel. The elongated body portion extends distally from the handle assembly. The head portion is disposed adjacent a distal end of the elongated body portion. The elongated channel extends through a majority of a length of the elongated body portion. A proximal opening of the elongated channel is disposed distally of a proximalmost end of the handle assembly. The method also includes the steps of positioning the surgical instrument adjacent a surgical site, and inserting a second surgical instrument through the proximal opening of the elongated channel and out of a distal opening of the elongated channel, such that at least a portion of the second surgical instrument is adjacent the surgical site.

DESCRIPTION OF THE DRAWINGS

Various embodiment of the presently disclosed surgical stapling device are disclosed herein with reference to the drawings, wherein.

DETAILED DESCRIPTION OF EMBODIMENTS

Embodiments of the presently disclosed surgical stapling instrument will now be described in detail with reference to the drawings in which like reference numerals designate identical or corresponding elements in each of the several views.

Throughout this description, the term "proximal" will refer to the portion of the instrument closer to the operator and the term "distal" will refer to the portion of the instrument further from the operator.

Figure 1:
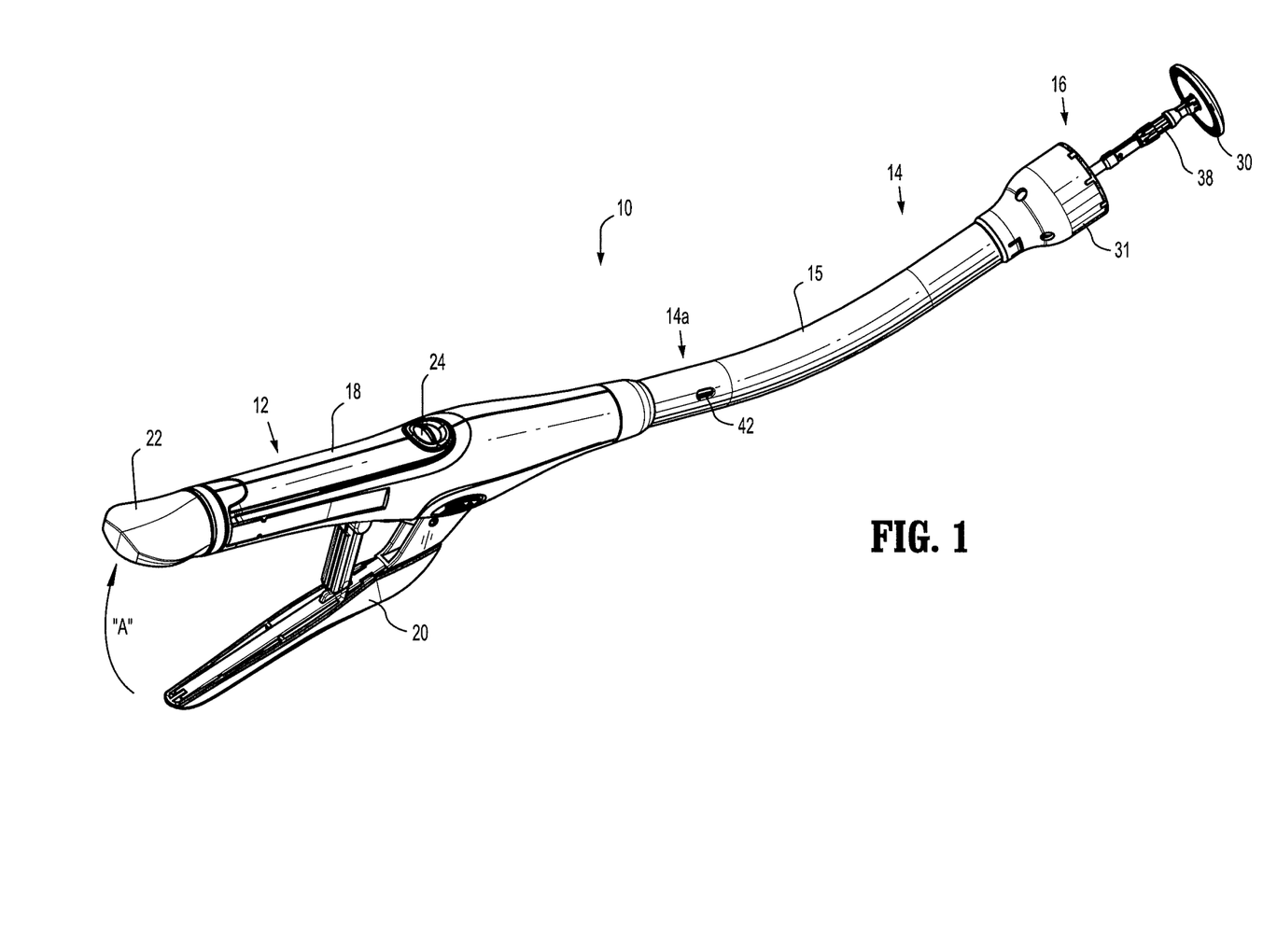
FIG. 1 is a perspective view of the presently disclosed surgical stapling instrument in an unapproximated position.

With initial reference to FIG. 1, an embodiment of the presently disclosed surgical stapling device is shown generally as reference number 10. Briefly, surgical stapling device 10 includes a handle assembly 12, an elongated body portion 14 including a curved elongated outer tube 15, and a head portion 16. Alternately, in some surgical procedures, e.g., the treatment of hemorrhoids, it is desirable to have a substantially straight body portion. The length, shape and/or the diameter of body portion 14 and head portion 16 may also be varied to suit a particular surgical procedure.

In the illustrated embodiments, handle assembly 12 includes a stationary handle 18, a firing trigger 20, a rotatable approximation knob 22 and an indicator 24. Head portion 16 includes an anvil assembly 30 and a shell assembly 31. Anvil assembly 30 is movable in relation to shell assembly 31 between spaced (unapproximated) and approximated positions. Anvil assembly includes an anvil shaft 34 mounted (preferably removably mounted) to the anvil retainer 38. An elongated channel 40 is disposed through a majority of the length of elongated body portion 14.

In operation, rotation of approximation knob 22 causes movement of anvil assembly 30 in relation to shell assembly 31 between spaced and approximated positions, as approximation knob 22 is mechanically engaged with anvil retainer 38 via bands 22, which is connected to anvil assembly 30. It is envisioned that rotation of approximation knob 22 in a first direction (e.g., clockwise) causes proximal movement of anvil assembly 30 to an approximated position and rotation of approximation knob 22 in a second opposite direction (e.g., counter-clockwise) causes distal movement of anvil assembly 30 to an unapproximated position.

Figure 10:
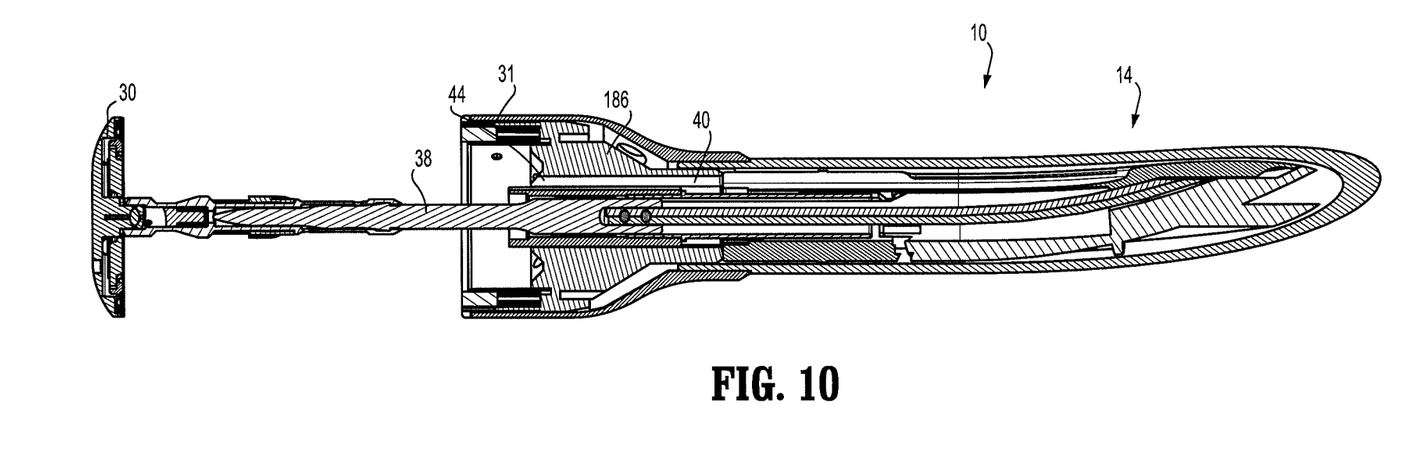
FIG. 10 is a longitudinal cross-sectional view of the surgical instrument of the present disclosure taken along line 10-10 of FIG. 9.
Figure 11:
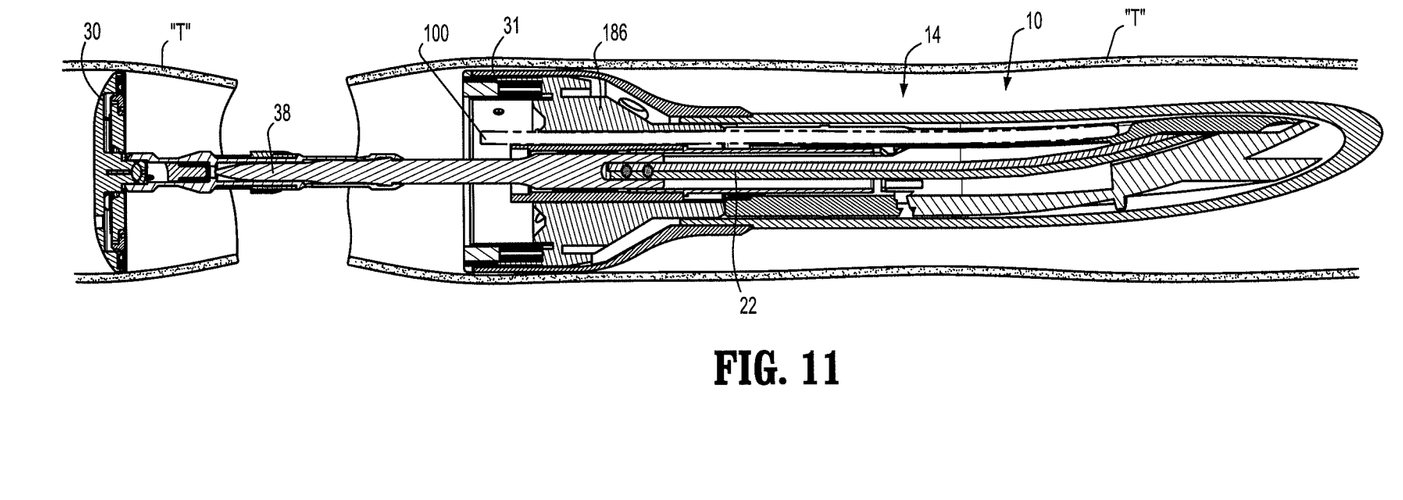
FIG. 11 is a view similar to FIG. 10 showing the instrument inserted into tissue and with a second surgical instrument inserted therethrough.

Actuation of firing trigger 20 (i.e., pivoting in the direction of arrow "A" in FIG. 1), causes staples to be ejected from shell assembly 31 towards anvil assembly 30. That is, firing trigger 20 is disposed in mechanical cooperation with a pusher 186 (see FIGS. 10 and 11) such that actuation of firing trigger 20 causes advancement of pusher 186 into contact with the staples, which forces the staples out of staple pockets 33 into staple deforming pockets of anvil assembly 30.

Further details of other features of surgical stapling device 10, such as the approximation assembly and firing assembly are disclosed in commonly-owned U.S. Pat. Nos. 7,303,106, 7,234,624 and 7,168,604, the entire contents of which are incorporated by reference herein.

Figure 2:
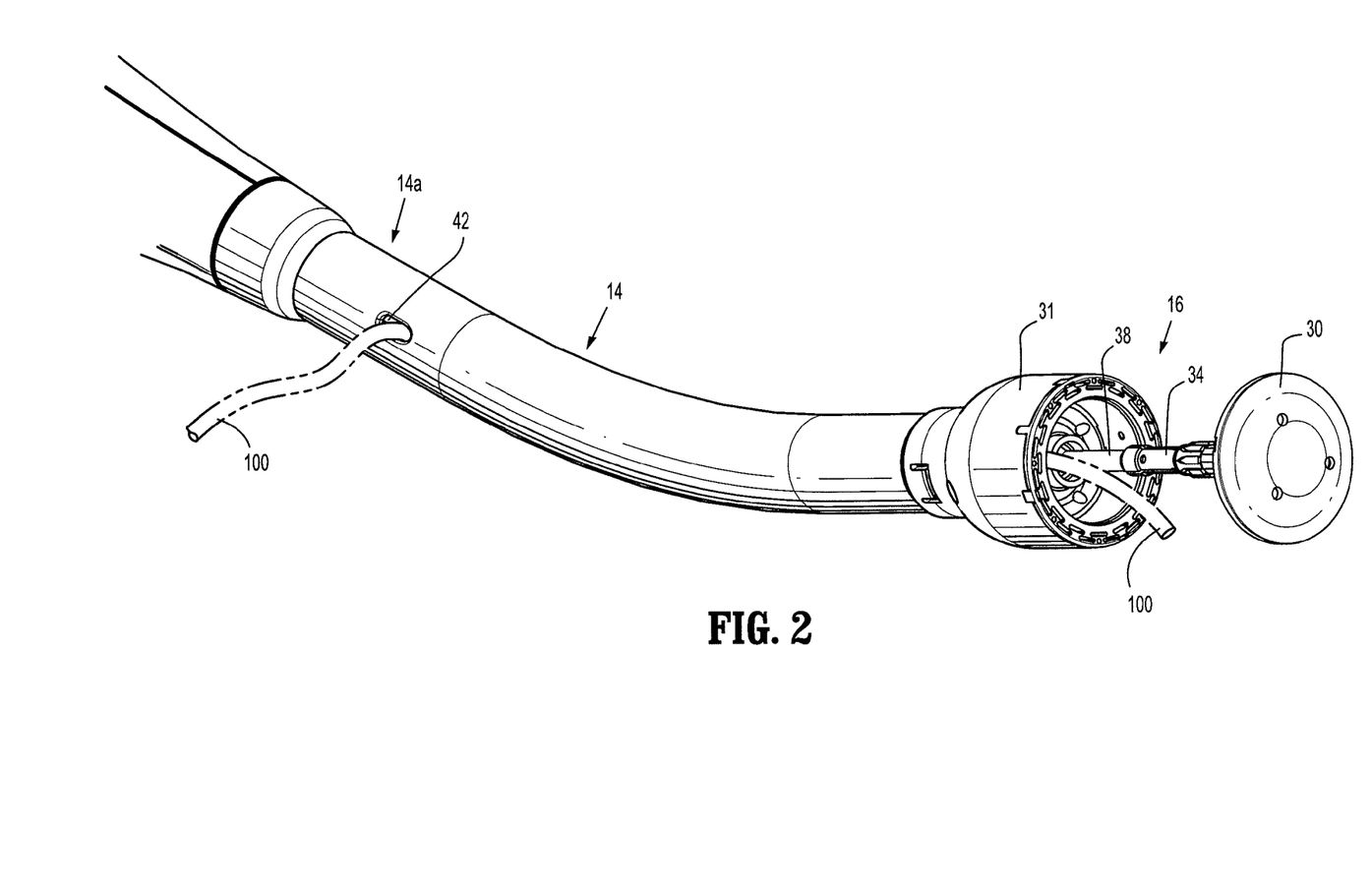
FIG. 2 is a perspective view of a portion of the surgical stapling instrument of FIG. 1 showing a second surgical instrument inserted therethrough.
Figure 3:
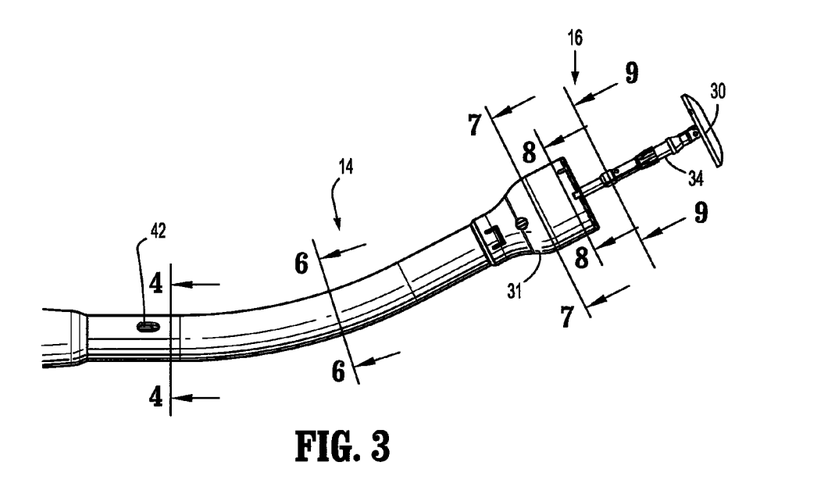
FIG. 3 is a side view of a portion of the surgical stapling instrument of FIG. 1.
Figure 4:
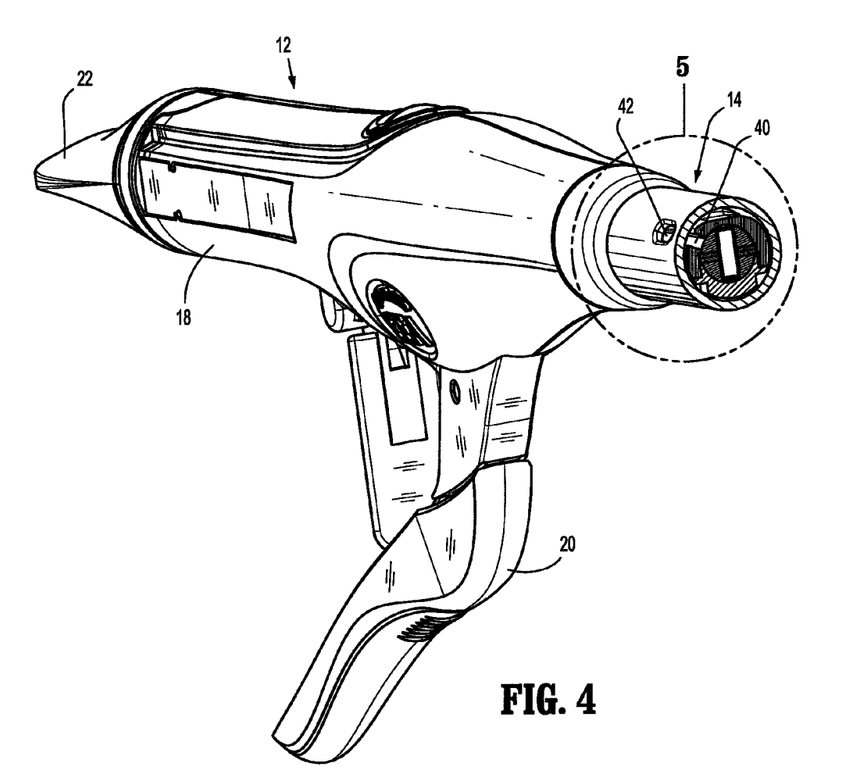
FIG. 4 is a perspective, partial cut-away view of the surgical instrument of the present disclosure showing a transverse cross-section along line 4-4 of FIG. 3
Figure 5:
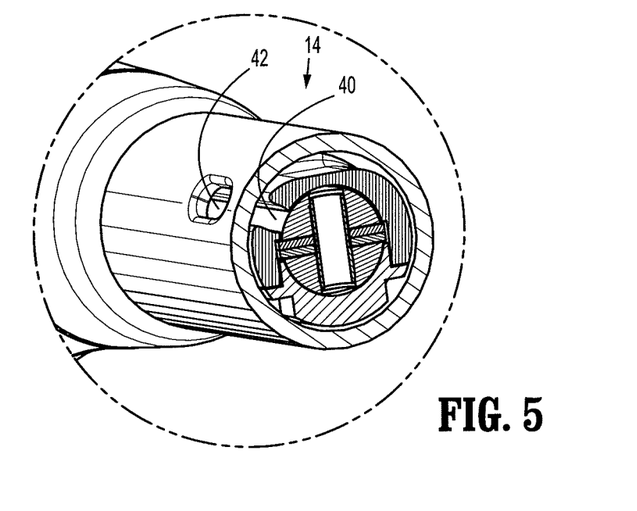
FIG. 5 is an enlarged view of the surgical instrument of the present disclosure in the indicated area of detail shown in FIG. 4.
Figure 6:
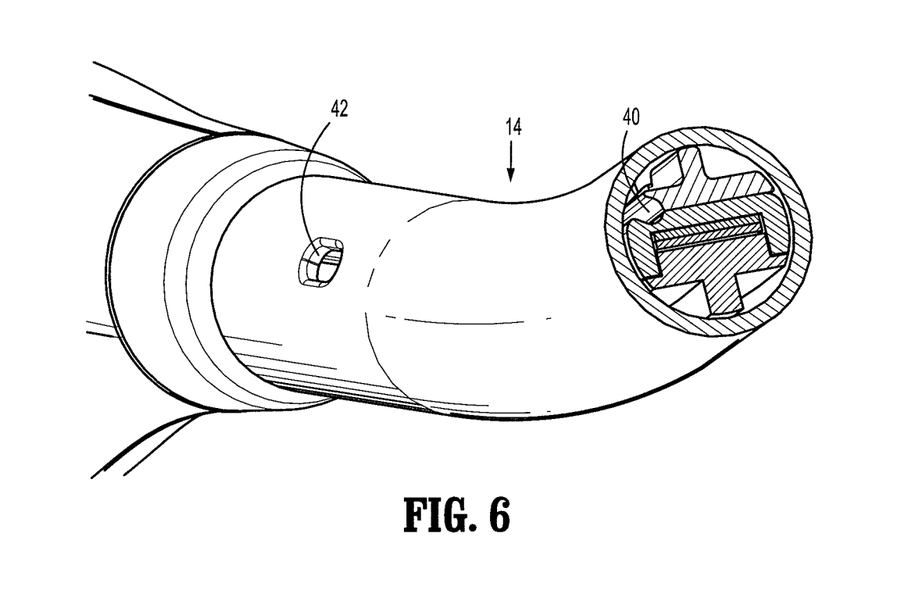
FIG. 6 is a perspective, partial cut-away view of the surgical instrument of the present disclosure showing a transverse cross-section along line 6-6 of FIG. 3.

In the illustrated embodiments, elongated channel 40 includes a proximal opening 42 (see FIGS. 2-6) and a distal opening 44 (see FIGS. 8-10) and is configured to allow another instrument 100 (FIG. 2) to pass therethrough. As shown, proximal opening 42 is disposed distally of a proximalmost end of the handle assembly 12 and proximal of the shell assembly 31, and preferably distally of the handle assembly 12 at a proximal portion 14a of elongated body portion 14 (i.e. proximally of the midpoint of the elongated body portion). Distal opening 44 is disposed on a distal-facing surface of shell assembly 31. The positioning of proximal opening 42 allows a second surgical instrument 100 to be inserted through surgical stapling device 10 and into tissue "T" (e.g., adjacent the surgical site; see FIG. 11). Since proximal opening 42 is disposed distally of handle assembly 12, elongated channel 40 does not interfere with any of the internal working components of handle assembly 12. Additionally, since proximal opening 42 is disposed at proximal portion 14a of elongated body portion 14, insertion of second surgical instrument 100 is facilitated when a distal portion of surgical stapling device 10 (e.g., head portion 16) is adjacent a target tissue site.

Figures 7, 8:
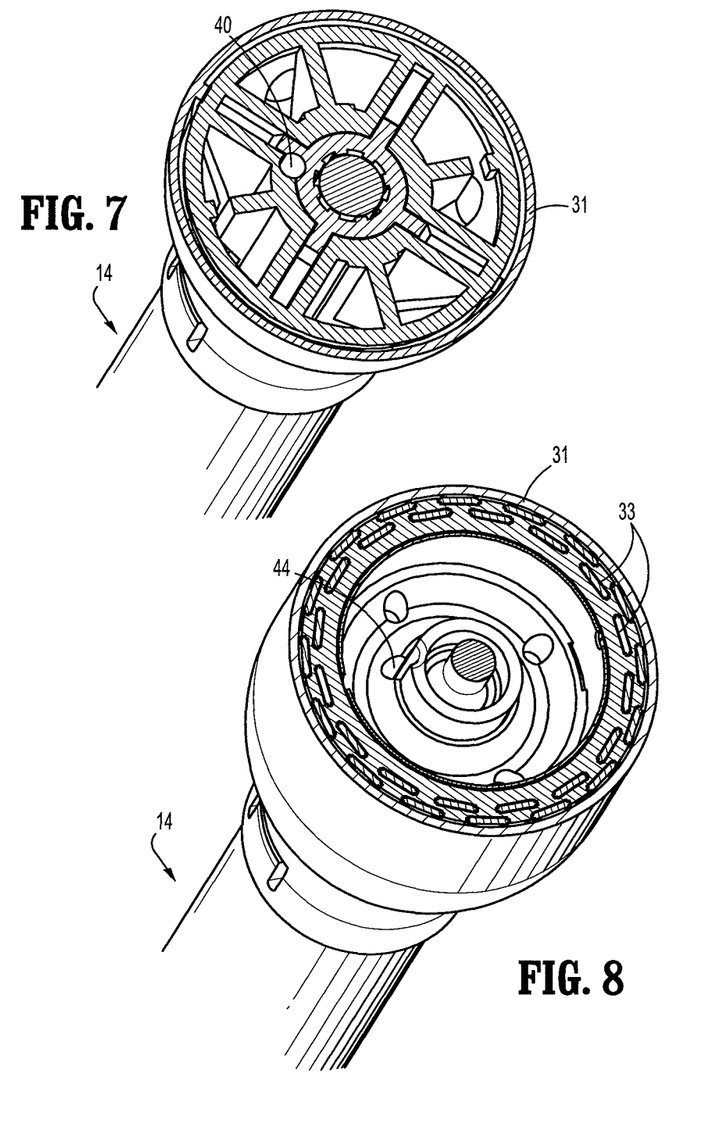
FIG. 7 is a perspective, partial cut-away view of the surgical instrument of the present disclosure showing a transverse cross-section along line 7-7 of FIG. 3.
FIG. 8 is a perspective, partial cut-away view of the surgical instrument of the present disclosure showing a transverse cross-section along line 8-8 of FIG. 3.
Figure 9:
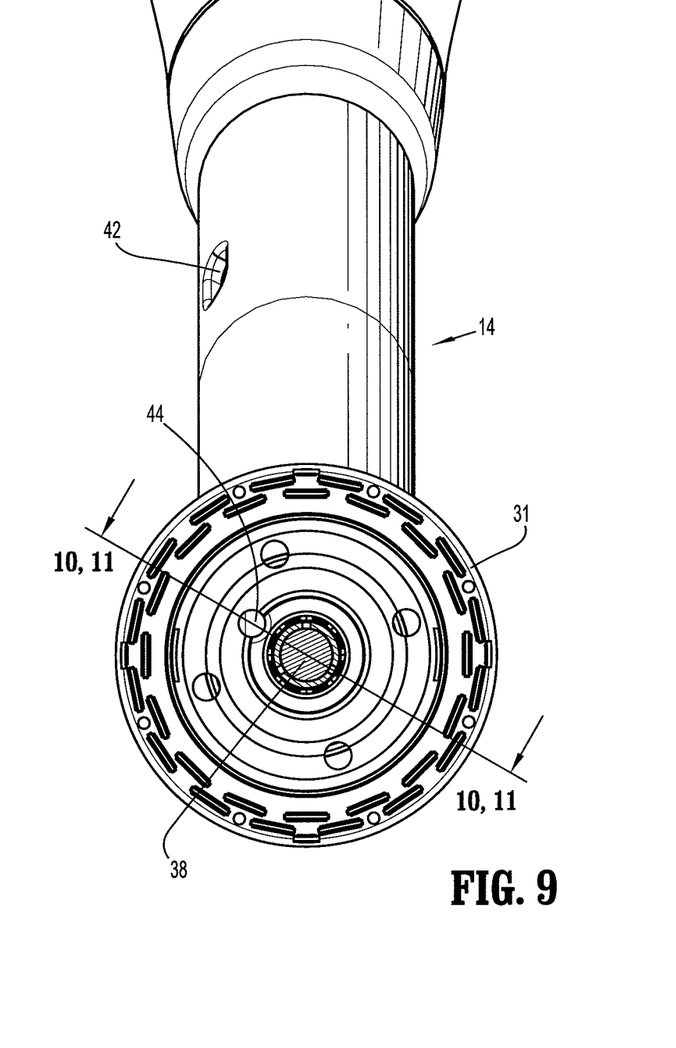
FIG. 9 is a perspective, partial cut-away view of the surgical instrument of the present disclosure showing a transverse cross-section along line 9-9 of FIG. 3.

With reference to FIGS. 7-9, distal opening 44 is displaced from an axial center (indicated by center of anvil retainer 38) of shell assembly 31 (see FIG. 9). This location of distal opening 44 helps ensure that elongated channel 40 does not interfere with the moving parts (e.g., pusher 186) of shell assembly 31. In one embodiment by way of example, the distal opening 44 is displaced in the range of about 0.20 inches to about 0.30 inches from the axial center of shell assembly 31. Other spacings are also contemplated.

Additionally, in FIGS. 1-3 and 6 elongated body portion 14 is illustrated having a longitudinally curved portion, which may be helpful for certain types of surgical procedures. While not explicitly illustrated, it is envisioned that elongated body portion 14 can include a bent portion or be substantially straight along its length. In embodiments where elongated body portion 14 is curved, elongated channel 40 may also include a curved portion, e.g., to accommodate a curved and/or flexible instrument.

In alternate embodiments where elongated body portion 14 is curved (or bent), elongated channel 40 may be substantially straight along its entire length. In these embodiments, it is envisioned that proximal opening 42 of elongated channel 40 is disposed proximally adjacent the bend or an apex of the curve, such that a straight, non-flexible surgical instrument can be inserted through elongated body portion 14 and out distal opening 44 to be adjacent the surgical site.

Elongated channel 40 is configured to allow a device to be passed therethrough, and in a preferred embodiment, is configured to allow an endoscope or an illumination device to pass therethrough. In such embodiments, a user is able to insert the endoscope and/or illumination device (e.g., to inspect staple lines) without having to remove surgical stapling device 10 from the patient. Additionally, fluids (e.g., saline or a leak-testing dye to verify staple line integrity) can be passed through elongated channel 40 to the surgical site. Also, flexible instruments can be inserted. In one embodiment, the diameter of elongated channel 40 is between about 0.115 inches and about 0.135 inches. Other dimensions are also contemplated.

The present disclosure also relates to a method of performing a surgical procedure. The method includes the steps of providing surgical instrument 10 (such as that described hereinabove), positioning surgical stapling device 10 adjacent a surgical site, and inserting second surgical instrument 100 through proximal opening 42 of elongated channel 40 and out of distal opening 44 of elongated channel 40, such that at least a portion of second surgical instrument 100 is adjacent the surgical site.

It will be understood that various modifications may be made to the embodiments disclosed herein. Therefore, the above description should not be construed as limiting, but merely as exemplifications of disclosed embodiments. For instance, while a specific type of a surgical stapling device is shown, other types of surgical devices are within the scope of the present disclosure. Those skilled in the art will envision other modifications within the scope and spirit of the claims appended hereto.

What is claimed:

1. A surgical stapling instrument, comprising:
   a handle assembly having a proximal-most end, the handle assembly being configured to be held during typical use of the surgical stapling instrument, the handle assembly having a tapered portion progressively tapering in a distal direction, the tapered portion terminating at a distal terminal end;
   an elongated body portion defining a longitudinal axis and extending distally from the handle assembly, the elongated body portion including side walls and a non-tapered diameter portion extending distally from the terminal end of the handle assembly, the elongated body portion having a constant diameter along its entire length;
   a head portion disposed adjacent a distal end of the elongated body portion and including an anvil assembly and a shell assembly; and
   an elongated channel including a proximal opening and a distal opening, the proximal opening being disposed in the side wall of the non-tapered diameter portion of the elongated body portion, distally of a terminal end of the handle assembly and proximally of a longitudinal midpoint of the elongated body portion, and the distal opening being disposed on the shell assembly, wherein substantially a majority of the elongated channel is completely surrounded by the side walls of the elongated body portion.

2. The instrument of claim 1, wherein the distal opening is displaced from an axial center of the shell assembly.

3. The instrument of claim 1, wherein the elongated body portion includes a longitudinally curved portion.

4. The instrument of claim 3, wherein the elongated channel includes a longitudinally curved portion.

5. The instrument of claim 1, wherein the proximal opening is disposed distal of the entire handle assembly.

6. The instrument of claim 1, wherein the shell assembly has a diameter greater than a diameter of the elongated body portion.

7. The instrument of claim 1, wherein the elongated channel is configured to allow at least one of an endoscope and an illumination device to pass through.

8. The instrument of claim 1, wherein a diameter of the elongated channel is between 0.115 inches and 0.135 inches.

9. The instrument of claim 1, wherein the proximal opening of the elongated channel is radially offset from a center of the elongated body.

10. The instrument of claim 1, wherein the elongated body portion extends from the handle assembly at a junction, wherein the junction is aligned with the longitudinal axis.

11. The instrument of claim 10, wherein the proximal opening of the elongated channel is disposed distally of the junction, and wherein the proximal opening of the elongated channel is offset from the longitudinal axis.

12. The instrument of claim 11, wherein the there is exactly one junction, and wherein the junction is the sole location wherein the elongated body portion contacts the handle assembly.

13. The instrument of claim 1, wherein the entire length of the elongated body portion is configured for insertion into a body.

14. The instrument of claim 1, wherein a portion of the proximal opening that is exposed to a user is flush with the associated side wall of the elongated body portion.

15. The instrument of claim 1, wherein the proximal opening of the elongated channel is formed on a circumferential wall of the elongated body portion, wherein the circumferential wall forms the radially outer-most boundary of the elongated body portion, and wherein the proximal-most opening is the initial opening to provide access to the surgical stapling instrument.

16. The instrument of claim 1, wherein the proximal opening of the elongated channel is disposed within a proximal-most longitudinal quarter of the elongated body portion.

17. The instrument of claim 1, further comprising a connection portion disposed between the handle assembly and the elongated body portion, wherein at least a portion of the connection portion includes a larger diameter than the elongated body portion.

18. The instrument of claim 1, wherein the handle assembly includes a connection portion disposed at its distal end, and where the elongated body portion extends distally from the connection portion.

19. The instrument of claim 1, wherein a distal-most edge of the proximal opening is disposed proximally of the longitudinal midpoint of the elongated body portion.

20. A surgical stapling instrument, comprising:
   a handle assembly;
   an elongated body portion defining a longitudinal axis and extending distally from the handle assembly, the elongated body portion having a constant diameter along its entire length;
   a head portion disposed adjacent a distal end of the elongated body portion and including an anvil assembly and a shell assembly; and
   an elongated channel including a proximal-most opening and a distal opening, the proximal-most opening being disposed in a side wall of the elongated body portion distally of the handle assembly and proximally of a longitudinal midpoint of the elongated body portion, the proximal-most opening being formed on a circumferential wall of the elongated body portion, the circumferential wall forming a radially outer-most boundary of the elongated body portion, the proximal-most opening is the initial opening to provide access by another instrument to the surgical stapling instrument, and the distal opening being disposed on the shell assembly, wherein a distal-most edge of the proximal opening being disposed proximally of the longitudinal midpoint of the elongated body portion.

21. The instrument of claim 20, wherein the elongated body portion includes a longitudinally curved portion.

22. The instrument of claim 20, wherein the entire length of the elongated body portion is configured for insertion into a body.

23. The instrument of claim 20, wherein the elongated body portion extends from the handle assembly at a junction, wherein the proximal opening of the elongated channel is disposed distally of the junction, and wherein the proximal opening of the elongated channel is offset from the longitudinal axis.

24. The instrument of claim 20, wherein a distal-most end of the elongated body portion and a proximal-most end of the elongated body portion have the same diameter.

25. The instrument of claim 20, wherein the proximal opening of the elongated channel is disposed within a proximal-most longitudinal quarter of the elongated body portion.

26. The instrument of claim 20, wherein a majority of the elongated channel between a proximal-most portion of the proximal opening and the distal opening is completely surrounded by the side wall of the elongated body portion.

27. A surgical instrument, comprising:
   a handle assembly;
   an endoscopic portion defining a longitudinal axis and disposed distally of the handle assembly, the endoscopic portion including a side wall, the endoscopic portion having a constant diameter along its entire length;
   a head portion disposed adjacent a distal end of the endoscopic portion and including an anvil assembly and a shell assembly; and
   an elongated channel including a proximal opening and a distal opening, the proximal opening being disposed in the side wall of a portion of the endoscopic portion having a constant diameter and proximally of a longitudinal midpoint of the endoscopic portion, and the distal opening being disposed on the shell assembly, a majority of the elongated channel between a proximal-most portion of the proximal opening and the distal opening being completely surrounded by the side walls of the endoscopic portion.

28. The surgical instrument of claim 27, wherein a distal-most edge of the proximal opening is disposed proximally of the longitudinal midpoint of the endoscopic portion.

* * * * *